US012692507B2

(12) United States Patent
Lai et al.

(10) Patent No.: US 12,692,507 B2
(45) Date of Patent: Jul. 28, 2026

(54) GENE ZmPLD3 FOR INDUCING MAIZE MATERNAL HAPLOID PRODUCTION AND ITS APPLICATION THEREOF

(71) Applicant: CHINA AGRICULTURAL UNIVERSITY, Beijing (CN)

(72) Inventors: Jinsheng Lai, Beijing (CN); Yuan Li, Beijing (CN); Weibin Song, Beijing (CN); Haiming Zhao, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 920 days.

(21) Appl. No.: 17/763,635

(22) PCT Filed: Jun. 15, 2020

(86) PCT No.: PCT/CN2020/096033
§ 371 (c)(1),
(2) Date: Mar. 24, 2022

(87) PCT Pub. No.: WO2021/063029
PCT Pub. Date: Apr. 8, 2021

(65) Prior Publication Data
US 2022/0333125 A1 Oct. 20, 2022

(30) Foreign Application Priority Data
Sep. 30, 2019 (CN) .......................... 201910938755.9

(51) Int. Cl.
*C12N 15/82* (2006.01)
*C12N 9/16* (2006.01)

(52) U.S. Cl.
CPC ........... *C12N 15/8218* (2013.01); *C12N 9/16* (2013.01); *C12Y 301/04004* (2013.01)

(58) Field of Classification Search
CPC .................................................. C12N 15/8218
USPC .......................................................... 800/285
See application file for complete search history.

(56) References Cited

PUBLICATIONS

Fourgoux-Nicol et al Plant Molecular Biology 40 :857-872 (Year: 1999).*
Yadav et al. Plant Gene 17:100165 (Year: 2019).*
First Office Action issued in corresponding Chinese Application No. 201910938755.9; mailed Nov. 30, 2021; 13 pgs.
International Search Report issued in corresponding International Application No. PCT/CN2020/096033; mailed Sep. 18, 2020; 8 pgs.

* cited by examiner

*Primary Examiner* — Li Zheng
(74) *Attorney, Agent, or Firm* — HAUPTMAN HAM, LLP

(57) ABSTRACT

A gene ZmPLD3 for inducing maize maternal haploid production and its application thereof. Transgenic homozygous mutant plants or their progeny can be obtained by knocking out the ZmPLD3 gene in maize, and maize maternal haploids can be produced by hybridizing them as paternal materials with other maize materials. A series of allelic mutations of the gene having maternal haploid induction function through hybridization were obtained. The experiments showed that the mutation of maize phospholipase PLD3 could lead to the production of maize maternal haploid, which provides new thoughts for revealing the biological role of phospholipase in maize maternal haploid induction process. At the same time, the mutant individuals have the maternal haploid induction ability in maize, which is of great significance for breeding new types of haploid induction lines with high haploid induction rate and improving the efficiency of maize haploid breeding.

11 Claims, 3 Drawing Sheets

Specification includes a Sequence Listing.

SEQUENCE LISTING

<160> NUMBER OF SEQ ID NOS: 12

<210> SEQ ID NO 1
<211> LENGTH: 3238
<212> TYPE: DNA
<213> ORGANISM: maize(Zea mays L.)

<400> SEQUENCE: 1

```
atgcagcgca ggagcggcga tgtccggact ccggacgctg ggtttgcgct gctccccacg       60
cggtttacta ttcctgatct ccttcccctt cctacgcatg gctccccgtc cattgctatg      120
ctccgccatt gtccacacac ctgcagccag ccttctgcct ttaaccccac cggcaatgtc      180
agtagtcttg atttcctagc ttccttcctt ccgctctctc actcctctgt aggtgcatcc      240
ttgttcttct tgcatcgtat cgatctgtcc atgccactgg agtctgtacg tacgttgcca      300
ttatacatgg gctctgtttg cgtatgtatg tgcaggtgac ctgatatcga cgggagggat      360
ggcaaggata ctgctccatg gttcgcttca tgtcaccatc tttgaggcag aggagctgtc      420
gaactccagc aggcccagca gccaggctcc cgggttcctc cgcaagctgg ttgaggggat      480
cgaggacact gtgggcgtgg gcaagggcac cagcaagatc tacgccacca tcgggctcgg      540
caagacccgc gtcggccgca cccgcaagct caccgacgag acggccagcc cgcgctggta      600
cgagtccttc cacgtctact gcgcccacct tgcctccgac gtcgtcttca ccatccgggc      660
caagaacccc atcggcgcct ccaccgtcgg tgtcgcctac ctccccgtcc gcgatatctt      720
cgagggccac gaggtggacc gctggctcca cctctgcgac ggcggcggcg acgacaagga      780
ccgcacgccg ctcgagagcg gcgggaaggt ccacgtcagg ctccagtact tcgacatctc      840
caaggaccac agctggggca agggcgtgcg cagtggaaag taccccggcg tgccctacac      900
cttcttctcg cagcggcagg ggtgcagggt gacgctgtac caggacgcgc acgtccccga      960
cggctttgtc ccgaggatcc cactcgacgg cggccggtgc tacgaggcgc accggtgctg     1020
```

```
ggaggacatc ttcgacgcca tcagcggcgc taagcacctc atctacatca cgggttggtc   1080
ggtgtacacg gagatcacgc tactcaggga cggcgcccgc ccacccaggc ccggcagcgg   1140
cgtcacgctc ggcgagctgc tcaagaagaa agccggcgag ggcgtccgtg tgctcatgct   1200
cgtctgggac gaccgcacct ccgtcggggc gctcaagaag gacgggctca tggccaccca   1260
cgacgaggag acgatgaact acttcgaggg caccgacgta cactgcgtgc tatgcccgcg   1320
aaaccccgac gactccggga gcatcgtgca ggacctgcag atctccacca tgttcacgca   1380
ccaccagaag atcgtcgtcg tcgaccacga catgccggtg cagcggtcgc agcggcagcg   1440
gaggatcctc agcttcgtgg gcgggctgga cctctgcgac ggccgctacg acacgccatg   1500
ccactcgctg ttccggacgc tggacggcgc gcaccacgac gacttccacc agccaaactt   1560
cgccacggcc gccatcgcca agggcggacc gagggagccg tggcacgaca tccactgtcg   1620
cctcgaaggc cccgtggcgt gggacgtgct ctacaacttc gagcagcggt ggcggaagca   1680
gggcggcaag gacttgctca tccagctccg ggacctcgcc gacgagatca tcgccccgtc   1740
acccgtcacg ttcccgaacg accccgagac gtggaacgtg cagctctttc gctctatcga   1800
cggcggcgcc gcgttcgggt tcccggacac ccccgacgac gccaccaggg ccgggctcgt   1860
cagtggcaag gaccagatca tcgatcggag catccaggac gcctacatcc acgccatccg   1920
ccgcgccagg agcttcatct acattgagaa ccagtacttc ctcggcagct cctactgctg   1980
gaagcccgac gggatcaagc ccgaggacat cggtgcactg cacgtcatcc ccaaggagct   2040
gtccatgaag gtggtgagca agatcgaggc cggcgagcgg ttcgcggtct acgtcgtggt   2100
gcccatgtgg cctgagggca tcccggagag cggctccgtg caggccatcc tcgactggca   2160
gaggaggacc atggagatga tgtacaccga catcgcacag gcgatccagg ccaaggggat   2220
cgacgccaac cccagggact acctcacctt cttctgcctc ggcaaccggg aggcgaagaa   2280
gccaggggag tacgtgccca cggaggaggc tgagcctgac actggctaca tcaaggccca   2340
gcaaaacaga aggttcatga tctatgtcca caccaagatg atgatgggta atccgtccgt   2400
ccacccttac tcctagaatt actcttgatt tttcgaattc gaggcgccca tcttcttaga   2460
atatattact cttgaattat tatcaaaatc gaaatttgct gtgtgtgcag tggatgacga   2520
gtacatcatc gtggggtcgg cgaacatcaa ccagcgttcc atggacgggg cgcgggactc   2580
ggagatcgcg atgggcgcgt accagccgca ccacctggcg gcggcgagca ggccggcgag   2640
agggcaggtg cacgggttcc ggatgtcgct gtggtacgag cacctgggcg cggtggacga   2700
cgcgttcacc cggccggaca gcgtcgagtg catccgcaag gtgaacgcca tggcagacag   2760
gtactgggac ctgtacgccg gcgacgggcc tgagcgtgac ctgccggggc acctgctcac   2820
ctatcccgtc gccgtcggca ctgacggctc ggtcaatcag ctgccgggga tggagttctt   2880
cccggacacg caggcgcggg tgcttggcgc caagtccgac tacctgccgc ccattctcac   2940
cacgtaggcg tgtgctctga gcctctcaca atctttttgga tttactgttt tccccattct   3000
ggacctgaat aagagcagaa ctagtttggt atttttttaaa aaagtaaata aaaggtgcac   3060
taatgcagtg tgcataatga cgaactcatt gttatttttag tattgtacta tcaattagta   3120 attttttaaaa tcgttgttta cctattgctg gtttgatagt gttttggtta gcttggctaa   3180
gaaccgagga gtcgtttggt tcacatatat ttgtaatgtg atggatagtt gagaacgt     3238
```

<210> SEQ ID NO 2
<211> LENGTH: 23
<212> TYPE: DNA
<213> ORGANISM: maize(Zea mays L.)

<400> SEQUENCE: 2
cgacatcgca caggcgatcc agg                                                     23

<210> SEQ ID NO 3
<211> LENGTH: 23
<212> TYPE: RNA
<213> ORGANISM: maize(Zea mays L.)

<400> SEQUENCE: 3
cgacaucgca caggcgaucc agg                                                     23

<210> SEQ ID NO 4
<211> LENGTH: 21
<212> TYPE: DNA
<213> ORGANISM: Artificial Sequence
<220> FEATURE:
<223> OTHER INFORMATION: Synthesized

<400> SEQUENCE: 4
cgccaggagc ttcatctaca t                                                      21

<210> SEQ ID NO 5
<211> LENGTH: 23
<212> TYPE: DNA
<213> ORGANISM: Artificial Sequence
<220> FEATURE:
<223> OTHER INFORMATION: Synthesized

<400> SEQUENCE: 5
catcatcatc ttggtgtgga cat                                                    23

<210> SEQ ID NO 6
<211> LENGTH: 96
<212> TYPE: RNA
<213> ORGANISM: Artificial Sequence
<220> FEATURE:
<223> OTHER INFORMATION: Synthesized

<400> SEQUENCE: 6
cgacaucgca caggcgaucc guuuuagagc uagaaauagc aaguuaaaau aaggcuaguc            60
cguuaucaac uugaaaaagu ggcaccgagu cggugc                                      96

<210> SEQ ID NO 7
<211> LENGTH: 23
<212> TYPE: DNA
<213> ORGANISM: Artificial Sequence
<220> FEATURE:
<223> OTHER INFORMATION: Synthesized

<400> SEQUENCE: 7
agaatctgtc cagtgtccga gcg                                                    23

<210> SEQ ID NO 8
<211> LENGTH: 23
<212> TYPE: DNA
<213> ORGANISM: Artificial Sequence
<220> FEATURE:
<223> OTHER INFORMATION: Synthesized

<400> SEQUENCE: 8
tatgaggaat cacatcccca acg                                                    23

<210> SEQ ID NO 9

-continued

```
<211> LENGTH: 27
<212> TYPE: DNA
<213> ORGANISM: maize(Zea mays L.)

<400> SEQUENCE: 9
cgacatcgca caggcgatcc aggccaa                                              27

<210> SEQ ID NO 10
<211> LENGTH: 60
<212> TYPE: DNA
<213> ORGANISM: maize(Zea mays L.)

<400> SEQUENCE: 10
ggagatgatg tacaccgaca tcgcacaggc gattccaggc caaggggatc gacgccaacc       60

<210> SEQ ID NO 11
<211> LENGTH: 59
<212> TYPE: DNA
<213> ORGANISM: maize(Zea mays L.)

<400> SEQUENCE: 11
ggagatgatg tacaccgaca tcgcacaggc gatccaggcc aaggggatcg acgccaacc        59

<210> SEQ ID NO 12
<211> LENGTH: 59
<212> TYPE: DNA
<213> ORGANISM: maize(Zea mays L.)

<400> SEQUENCE: 12
ggagatgatg tacaccgaca tcgcacaggc gatccaggcc aaggggatcg acgccaacc        59
```

GENE ZmPLD3 FOR INDUCING MAIZE MATERNAL HAPLOID PRODUCTION AND ITS APPLICATION THEREOF

RELATED APPLICATIONS

The present application is a U.S. National Phase of International Application Number PCT/CN2020/096033 filed Jun. 15, 2020 and claims priority to Chinese Application Number 201910938755.9 filed Sep. 30, 2019.

INCORPORATION BY REFERENCE

The sequence listing provided in the file entitled Amended_SQL.txt, which is an ASCII text file that was created on Mar. 17, 2022, and which comprises 6,326 bytes, is hereby incorporated by reference in its entirety.

TECHNICAL FIELD

The present invention relates to gene ZmPLD3 for inducing maize maternal haploid production and its application thereof.

BACKGROUND

Maize is one of the important crops in the world and the most widely grown crop in China. The rapid growth of the world population and climate change have put forward higher requirements for the breeding of high-yield and multi-resistant high-quality maize hybrid varieties. The selection of excellent inbred lines is very important for breeding hybrids. Compared with the time-consuming and labor-intensive conventional breeding methods, the hybrid induction-based maize haploid breeding method needs only two generations to quickly obtain pure lines, which greatly shortens the breeding process and is one of the important modern breeding techniques. The basic procedure for conventional haploid breeding is to obtain haploids by crossing the haploid induction line as the male parent to the ordinary female parent material, and then form a doubled haploid pure line by doubling. At present, the common haploid induction lines are mainly maternal haploid induction lines, and stock6 is the first maize maternal induction line found. Using induction lines from stock6 can obtain a certain proportion of haploids on almost all female parent materials. Breeders from all over the world have selected a large number of excellent induction lines based on this, and the induction rate has also been increasing.

With the large-scale application of induction lines in breeding practice, the research on the genetic mechanism of haploid induction has also been deepened. By mining related genes, identifying more genes that regulate haploid induction, and further increasing the induction rate, is of great significance for breeding a new type of induction line with high induction rate and the analysis of the genetic mechanism of haploid induction.

SUMMARY OF THE INVENTION

The present invention provides a gene ZmPLD3 for inducing maize maternal haploid production and its application thereof.

In the first aspect, the present invention protects a method for producing plant maternal haploids, which comprises the following steps:

(1) Silence or suppress the expression of the ZmPLD3 gene in the target plant genome or knock out the ZmPLD3 gene to obtain a transgenic plant; (2) Cross the transgenic plant as described in step (1) or its offspring as the male parent with other plants to obtain the hybrid offsprings which are maternal haploids;

ZmPLD3 gene mentioned above is any one of the following DNA molecules:

(1) The DNA molecule whose genome sequence is as shown in SEQ ID NO: 1 of the sequence listing;

(2) DNA molecule that hybridizes to DNA molecules defined in (1) under stringent conditions and encode proteins with the same function;

(3) DNA molecule that originated from maize, whose sequence is 90%, 91%, 92%, 93%, 94%, 95%, 96%, 97%, 98% or 99% identical to the DNA sequence defined in (1) or (2) and with the same function.

Silencing or suppressing the expression of ZmPLD3 gene in the target plant genome or knocking out ZmPLD3 gene, is to mutate the ZmPLD3 gene in the target plant genome to reduce the expression of the ZmPLD3 gene in the target plant genome or cause the ZmPLD3 gene in the target plant genome to lose function.

Reducing the expression of the ZmPLD3 gene in the target plant genome or causing the ZmPLD3 gene in the target plant genome to lose function mentioned above is achieved by the following way: Mutate the first exon and/or the second exon and/or the third exon of the ZmPLD3 gene in the target plant genome; Above-mentioned mutation is a deletion mutation and/or an insertion mutation and/or a substitution mutation.

Above-mentioned mutation is to insert the base T between the 2205th base and the 2206th base of the 5'end of the ZmPLD3 gene in the target plant genome. In the embodiments of the present invention, above-mentioned mutation occurs on both homologous chromosomes of the target plant.

Above-mentioned mutation is achieved by CRISPR/Cas9 gene editing technology; the target sequence of the CRISPR/Cas9 is as shown in SEQ ID NO: 2 of the sequence listing. The sgRNA sequence of above-mentioned CRISPR/Cas9 is as shown in SEQ ID NO: 3 of the sequence listing.

The full-length sgRNA sequence of above-mentioned CRISPR/Cas9 is shown in SEQ ID NO: 6 of the sequence listing.

Inserting the base T between the 2205th base and the 2206th base of the 5'end of the ZmPLD3 gene in the target plant genome mentioned above comprises the following steps: Transfer the CRISPR/Cas9 vector expressing above-mentioned sgRNA into the target plant to obtain a transgenic plant. Above-mentioned CRISPR/Cas9 vector may specifically be a recombinant vector obtained by inserting the DNA molecule shown as SEQ ID NO: 2 into the Esp3I site of the sgRNA-Cas9 dual expression vector.

Crossing the transgenic plant or its offspring as the male parent with other plants in step (1) refers to: Use the transgenic plant or its offspring in step (1) as the male parent and other plants as the female parent to cross.

The "obtaining the hybrid offsprings which are maternal haploids" refers to selecting and obtaining the maternal haploids from the hybrid offspring.

The "selecting and obtaining the maternal haploids from the hybrid offspring" is achieved by the following method: Individual plants of the hybrid offspring are screened by haploid phenotypic identification and/or ploidy identification and/or molecular marker identification.

The "selecting and obtaining the maternal haploids from the hybrid offspring" is achieved by the following method: Individual plants of the hybrid offspring are screened by ploidy identification and molecular marker identification.

The "selecting and obtaining the maternal haploids from the hybrid offspring" is achieved by the following method: Individual plants of the hybrid offspring are screened by haploid phenotypic identification.

The "selecting and obtaining plant maternal haploid from the hybrid offspring" is achieved by the following method: Individual plants of the hybrid offspring are screened by haploid phenotypic identification and ploidy identification and molecular marker identification.

Molecular marker identification can be specifically: If a hybrid offspring has a maternal-specific molecular marker and does not have a paternal-specific molecular marker, the hybrid offspring individual is a candidate for the maternal haploids.

Ploidy identification can be specifically: Using flow cytometry to detect, if the cell nucleus of the hybrid offspring has a haploid cell nuclear signal peak, the hybrid offspring is a candidate for the maternal haploids.

Haploid trait identification can be specifically: If a hybrid offspring individual has the phenotype of short stalk, narrow leaves, small plant shape and male sterility, the hybrid offspring is a candidate for the maternal haploids. Above-mentioned phenotype is compared with the phenotype of the diploids in the hybrid offspring.

Above-mentioned step (2) also includes the following steps: Individual plants of the hybrid offspring are screened by haploid phenotypic identification and/or leaf ploidy identification and/or molecular marker identification, and the individual plants identified as haploid by any method are selected as the maternal haploids.

In the second aspect, the present invention protects a method for preparing a maternal haploid induction line, which is to silence or suppress the expression of the ZmPLD3 gene in the target plant genome or knock out the ZmPLD3 gene to obtain a transgenic plant which is a maternal haploid induction line.

Above-mentioned ZmPLD3 gene is as described above.

Silencing or suppressing the expression of ZmPLD3 gene in the target plant genome or knocking out ZmPLD3 gene, is to mutate the ZmPLD3 gene in the target plant genome to reduce the expression of the ZmPLD3 gene in the target plant genome or cause the ZmPLD3 gene in the target plant genome to lose function.

Reducing the expression of the ZmPLD3 gene in the target plant genome or causing the ZmPLD3 gene in the target plant genome to lose function mentioned above is achieved by the following way: Mutate the first exon and/or the second exon and/or the third exon of the ZmPLD3 gene in the target plant genome; Above-mentioned mutation is a deletion mutation and/or an insertion mutation and/or a substitution mutation.

Above-mentioned mutation is to insert the base T between the 2205th base and the 2206th base of the 5'end of the ZmPLD3 gene in the target plant genome. In the embodiments of the present invention, above-mentioned mutation occurs on both homologous chromosomes of the target plant.

Above-mentioned mutation is achieved by CRISPR/Cas9 gene editing technology; The target sequence of the CRISPR/Cas9 is as shown in SEQ ID NO: 2 of the sequence listing. The sgRNA sequence of above-mentioned CRISPR/Cas9 is as shown in SEQ ID NO: 3 of the sequence listing.

The full-length sgRNA sequence of above-mentioned CRISPR/Cas9 is shown in SEQ ID NO: 6 of the sequence listing.

Inserting the base T between the 2205th base and the 2206th base of the 5'end of the ZmPLD3 gene in the target plant genome mentioned above comprises the following steps: Transfer the CRISPR/Cas9 vector expressing above-mentioned sgRNA into the target plant to obtain a transgenic plant. Above-mentioned CRISPR/Cas9 vector may specifically be a recombinant vector obtained by inserting the DNA molecule shown as SEQ ID NO: 2 into the Esp3I site of the sgRNA-Cas9 dual expression vector.

In the third aspect, the present invention protects the maternal haploids produced by the method described in the first aspect.

In the fourth aspect, the present invention protects the maternal haploid induction line prepared by the method described in the second aspect.

In the fifth aspect, the present invention protects a specific sgRNA for CRISPR-Cas9 gene editing; The target sequence of the CRISPR/Cas9 is as shown in SEQ ID NO: 2 of the sequence listing. The sgRNA sequence of above-mentioned CRISPR/Cas9 is as shown in SEQ ID NO: 3 of the sequence listing.

The full-length sgRNA sequence of above-mentioned CRISPR/Cas9 is shown in SEQ ID NO: 6 of the sequence listing.

In the sixth aspect, the present invention protects a vector for CRISPR-Cas9 gene editing which expresses specific sgRNA; The target sequence of the sgRNA is as shown in SEQ ID NO: 2 of the sequence listing. Above-mentioned CRISPR/Cas9 vector may specifically be a recombinant vector obtained by inserting the DNA molecule shown as SEQ ID NO: 2 into the Esp3I site of the sgRNA-Cas9 dual expression vector.

In the seventh aspect, the present invention protects any of the following applications:

(A) Application of substances used to silence or suppress the expression of ZmPLD3 gene or knock out ZmPLD3 gene in the target plant genome to the production of maternal haploids;

(B) Application of substances used to silence or suppress the expression of ZmPLD3 gene or knock out ZmPLD3 in the target plant genome gene to the selection and breeding of new induction lines with high haploid induction rate and/or improving the efficiency of maize haploid breeding;

(C) Application of any method in the first aspect and the second aspect to the selection and breeding of new haploid induction lines with high haploid induction rate and/or improving the efficiency of maize haploid breeding;

(D) Application of the maternal haploids obtained by any one of the methods in the first aspect to the selection and breeding of new haploid induction lines with high haploid induction rate and/or improving the efficiency of maize haploid breeding;

The ZmPLD3 gene is as described forementionedly.

The substance for silencing or suppressing the expression of the ZmPLD3 gene or knocking out the ZmPLD3 gene in the target plant genome may specifically be a CRISPR/Cas9 knockout vector; the target sequence of above-mentioned CRISPR/Cas9 knockout vector is as shown in SEQ ID NO: 2 of the sequence listing; The sgRNA sequence of above-mentioned CRISPR/Cas9 is as shown in SEQ ID NO: 3 of the sequence listing. The full-length sgRNA sequence of above-mentioned CRISPR/Cas9 is shown in SEQ ID NO: 6 of the sequence listing. Above-mentioned CRISPR/Cas9 knockout vector may specifically be a recombinant vector obtained by inserting the DNA molecule shown as SEQ ID NO: 2 into the Esp3I site of the sgRNA-Cas9 dual expression vector.

Any of the aforesaid plants is (A1) or (A2) or (A3):

(A1) Dicots or monocots;

(A2) Gramineae;

(A3) Maize.

When the target plant is maize inbred line B73 and other plant is maize inbred line Mo17: Using the plant genomic DNA as template, and a primer pair composed of Indel-F and Indel-R to perform PCR amplification, if there is an amplified product (approximately 400 bp) corresponding to the male parent, then the plant has a paternal-specific molecular marker; if there is a maternal corresponding amplified product (approximately 300 bp), the plant has a maternal-specific molecular marker.

The basic principle of the present invention is as follows: For the ZmPLD3 gene, a target site sequence is designed on its second exon for the CRISPR/Cas9 site-directed mutagenesis, and mutation in the second exon of the gene is screened to obtain transgenic mutants with loss of gene function. Mutated T0 plants are self-pollinated to obtain T1 generation seeds. Plant the seeds, and the pollen of the homozygous mutants in the T1 generation is used to pollinate the maize inbred line Mo17 to obtain the hybrid offspring. The hybrid offspring are planted in the field, and identified by the field phenotype and/or molecular markers and/or flow cytometry ploidy identification and so on to verify whether they are maternal haploids.

EMBODIMENTS

The following examples facilitate a better understanding of the present invention, but do not limit the present invention. The experimental methods in the following examples were conventional methods unless otherwise specified. The experiment materials used in the following examples, unless otherwise specified, were all purchased from conventional biochemical reagent stores. The quantitative tests in the following examples were all set to three repeated tests, and the results were averaged.

sgRNA-Cas9 dual expression vector: recorded in the literature: Zhu J, Song N, Sun S, Yang W, Zhao H, Song W, Lai J. Efficiency and Inheritance of targeted mutagenesis in maize using CRISPR-Cas9. *J Genet Genomics*. 2016; 43:25-36.; the public can get it from China Agricultural University.

maize B73 (maize inbred line B73): recorded in the literature: Schnable, P. S. et al. The B73 maize genome: complexity, diversity, and dynamics. Science. 2009; 326: 1112-1115.; the public can get it from China Agricultural University.

maize Mo17 (maize inbred line Mo17): recorded in the literature: Sun S, Zhou Y, Chen J, Shi J, Zhao H, Zhao H, Song W, Zhang M, Cui Y, Dong X, Liu H, Ma X, Jiao Y, Wang B, Wei X, Stein J C, Glaubitz J C, Lu F, Yu G, Liang C, Fengler K, Li B, Rafalski A, Schnable P S, Ware D H, Buckler E S, Lai J. Extensive intraspecific gene order and gene structural variations between Mo17 and other maize genomes. *Nature Genetics*. 2018; 50 (9): 1289-1295.; the public can get it from China Agricultural University.

Example 1. Gene ZmPLD3 Inducing Maize Maternal Haploid Production and its Application The genome sequence of the wild-type maize ZmPLD3 gene is shown in SEQ ID NO: 1 of the sequence listing, its first exon is shown in SEQ ID NO: 1 of the sequence listing from positions 1-232 from the 5'end, its second exon is shown in SEQ ID NO: 1 of the sequence listing from positions 336-2387 from the 5'end, and its third exon is shown in SEQ ID NO: 1 of the sequence listing from positions 2511-2947 from the 5'end.

1. The CRISPR/Cas9 System to Knock Out the Maize ZmPLD3 Gene

Figure 1:
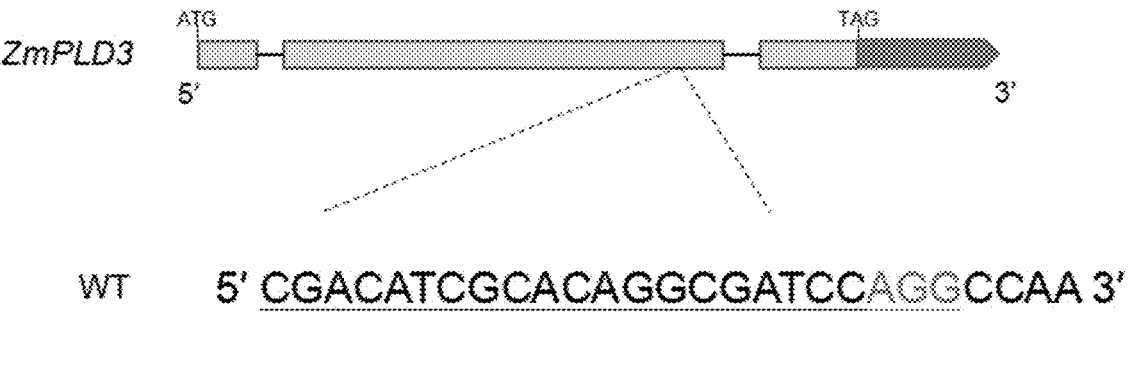
FIG. 1 is a schematic diagram of ZmPLD3 gene structure and CRISPR/Cas9 system knocking out target site (target sequence is underlined). The nucleotide sequence shown in FIG. 1 is SEQ ID NO:9.
Figure 1:

The schematic diagram of ZmPLD3 gene structure and the target site of CRISPR/Cas9 system are shown in FIG. 1.

(1) The target site was designed on the second exon of the maize ZmPLD3 gene, and its length is 23 bp.

```
Target site sequence:
                              (SEQ ID NO: 2)
5'-CGACATCGCACAGGCGATCCAGG-3'.

Corresponding sgRNA sequence of
target site design:
                              (SEQ ID NO: 3)
5'-CGACAUCGCACAGGCGAUCCAGG-3'.
```

(2) The double-stranded DNA molecule shown in SEQ ID NO: 2 was inserted into the Esp3I site of the sgRNA-Cas9 dual expression vector to obtain the CRISPR/Cas9 knockout vector (verified by sequencing). The full-length sgRNA expressed by the CRISPR/Cas9 knockout vector is shown in SEQ ID NO: 6 of the sequence listing.

(3) The CRISPR/Cas9 knockout vector prepared in step (2) was transformed into competent cells of *Agrobacterium* EHA105 to obtain recombinant strain EHA105/CRISPR/Cas9. Then the recombinant strain EHA105/CRISPR/Cas9 was transformed into immature embryos of maize B73 by the method of *Agrobacterium*-mediated infection (recombinant *Agrobacterium* was reproduced at 28° C., and the reproduced bacterial solution was used to infect maize immature embryos), and the maize B73 immature embryos were screened and differentiated. After screening, differentiation and rooting, T0 transgenic maize plants were obtained.

(4) The leaves of each T0 transgenic maize plant obtained in step (3) were collected respectively, and genomic DNA was extracted as template. PCR amplification was performed with primer pair consisting of primer check-F and primer check-R to obtain amplified products of different T0 transgenic maize plants.

```
check-F:
                                          (SEQ ID NO: 4)
5'-CGCCAGGAGCTTCATCTACAT-3';

check-R:
                                          (SEQ ID NO: 5)
5'-CATCATCATCTTGGTGTGGACAT-3'.
```

The PCR amplification products of different T0 transgenic maize plants were sequenced respectively, and the sequencing results were compared with the reference sequence of the second exon of wild-type maize ZmPLD3 gene to identify whether mutation of the gene ZmPLD3 in different T0 transgenic maize plants had been achieved.

Figure 2:
FIG. 2 is the sequencing comparison result of ZmPLD3 mutant gene zmpld3-1 and wild-type ZmPLD3 gene in maize. The partial nucleotide sequence of zmpld3-1 is SEQ ID NO:10. The partial nucleotide sequence of wild-type ZmPLD3 gene is SEQ ID NO:11. The alignment result of SEQ ID NO: 10 and SEQ ID NO: 11 is shown in SEQ ID NO: 12.

The results were as follows: Among the 7 T0 transgenic maize plants, one mutated plant was identified (named the ZmPLD3 mutant gene zmpld3-1). The specific mutation was shown in FIG. 2, whose difference between the ZmPLD3 mutant gene zmpld3-1 and the wild-type maize ZmPLD3 gene only was the insertion of the base T between the 2205th base and the 2206th base from the 5'end of SEQ ID NO: 1 in the sequence listing.

The plant with mutation in the aforesaid gene was recorded as positive T0 transgenic maize plant.

(5) The positive T0 transgenic maize plant obtained from step (4) was cultivated, self-pollinated and harvested, and the seeds were cultivated into plants to obtain T1 transgenic maize plants. To identify whether gene ZmPLD3 of T1 transgenic maize plants was a mutant genotype, the specific method was as follows: Using the genomic DNA of the leaves from T1 generation transgenic maize plants as a template, the primer pair consisting of primer check-F and primer check-R was used for PCR amplification, the PCR products were sequenced to classify the genotypes of T1 transgenic maize plants based on the sequencing results.

According to the sequencing results: (1) The sequence with bimodal characteristics of the target site was the heterozygous genotype, and T1 transgenic maize plant was heterozygous mutant (the gene was mutated in one homologous chromosome, and was not mutated in the other homologous chromosome). (2) The sequence with single-peak characteristics of the target site was compared with the second exon sequence of the maize wild-type ZmPLD3 gene. If it was the same, its corresponding plant was wild-type and no mutation occurred, and the following analysis would not consider it. If mutation occurred, which was obtained by the T0 transgenic plant self-pollinated, it was identified as the homozygous genotype and corresponding T1 transgenic maize plants was homozygous mutant (the ZmPLD3 gene was mutated in both homologous chromosomes).

After analysis, the homozygous mutated transgenic maize plants in T1 generation included zmpld3-1, and the mutation type was as following: Both homologous chromosomes of the homozygous mutated transgenic maize plants in T1 generation contained the mutant gene zmpld3-1 (the only difference between zmpld3-1 and the wild-type maize ZmPLD3 gene was that the base T was inserted between the 2205th base and the 2206th base from the 5'end of SEQ ID NO: 1 in the sequence listing).

2. Identification of the Haploid Inducibility of the Mutant Obtained by Knocking Out the ZmPLD3 Gene of Maize by CRISPR/Cas9 System (1) Polymorphic Molecular Marker Identification 10 pairs of molecular markers were designed with the maize B73 reference genome, and B73 and Mo17 genomic DNA were used as templates for amplification and polymorphic molecular marker screening, and finally 1 pair of molecular marker was chosen for further analysis (the primer pair was composed of Indel-F and Indel-R; Indel-F was shown as SEQ ID NO: 7; Indel-R was shown as SEQ ID NO: 8; Indel-F: AGAATCTGTCCAGTGTCCGAGCG; Indel-R: TATGAGGAATCACATCCCCAACG). The PCR product of B73 was about 400 bp, while the PCR product of Mo17 was about 300 bp. There was a big difference which could be distinguished by agarose gel electrophoresis. The PCR product of B73 was larger and the electrophoresis speed was slow, while the product fragment of Mo17 was smaller and the electrophoresis speed was fast. Therefore, the band of B73 was located above the Mo17 band (in FIG. 5, the first lane was the Mo17 band, and the second lane was B73 band). If the tested individual plant had only the band of Mo17 (lanes 4 and 5 in FIG. 5), it was considered as the maternal haploid, which did not have the band type of the male parent. If there were both B73 and Mo17 bands in the same lane (the third lane in FIG. 5), its corresponding individual plant was considered as the diploid of hybrid offspring.

The pollen of T1 transgenic homozygous mutant line zmpld3-1 was used to pollinate the inbred line Mo17 to obtain hybrid offspring. The hybrid progenies obtained were planted in greenhouse, and leaves of 14-day-old seedling were taken for genomic DNA extraction and agarose banding detection. The molecular marker identification results were as follows:

Among the 195 hybrid offsprings of the T1 transgenic homozygous mutant line zmpld3-1 and the inbred line Mo17, we obtained 2 individuals with only Mo17 band, which were identified as haploids (named haploid candidates).

Figure 5:
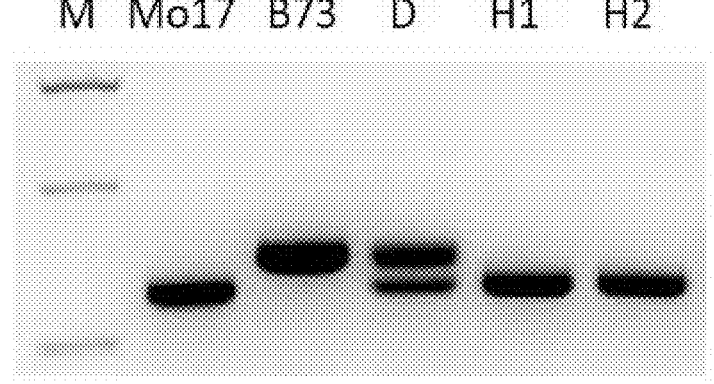
FIG. 5 is the results of haploid identification via polymorphic molecular markers.

The gel electrophoresis results of PCR products of 2 haploid candidates were shown in FIG. 5: M, marker, Mo17 meant Mo17 band type, B73 meant B73 band type, D was the diploid band type in the offspring, H1 and H2 were the haploid band type in the offspring.

(2) Ploidy Identification Via Flow Cytometry

Ploidy identification of the 2 haploid candidates conformed in aforesaid (1) was performed via flow cytometry, and the method was as follows: Extracted the nucleus from the young leaves of the tested plant, and used diploid maize leaves as a control, then used flow cytometry to detect the ploidy. First the nuclear signal peak of diploid control was set at 400 (since the content of genetic material in diploid cells is twice of that in haploid cells, the nuclear signal peak of haploid cells appeared at around 200). If the signal peak of the tested plant appeared at 400, it was considered as diploid. If the nuclear signal peak of the tested plant appeared at 200, the tested plant was considered as haploid.

Figure 4:
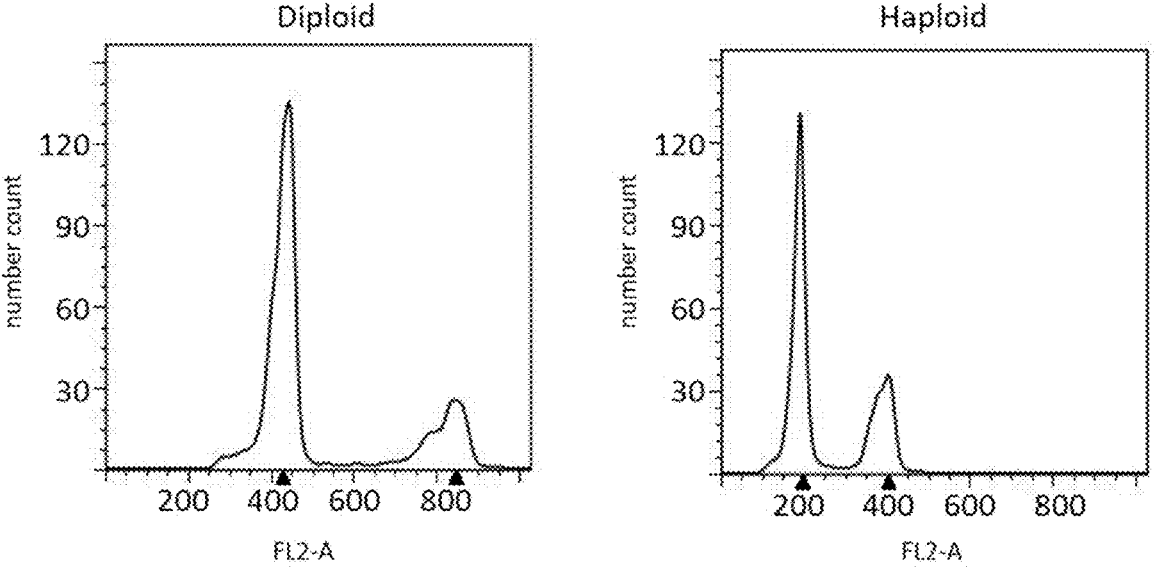
FIG. 4 is the results of ploidy identification via flow cytometry.

The results were shown in FIG. 4, the left image was the flow cytometry result of B73 wild-type maize, and the right image was the flow cytometry result of haploid candidates obtained by crossing the homozygous mutant line zmpld3-1 of the T1 transgenic maize plants to the maize inbred line Mo17.

The results showed that the ploidy of two haploid candidates identified by polymorphic molecular markers in the hybrid progeny of zmpld3-1 and inbred line Mo17 was haploid, which was conformed by flow cytometry.

(3) Phenotypic Identification

The phenotype of two haploid candidates, obtained by crossing the homozygous mutant line zmpld3-1 of the T1 generation transgenic maize plants to the maize inbred line Mo17, was continuously observed. Haploid had the characteristics of short stalk, narrow leaves, small plant shape and male sterility. Diploid was characterized by tall stalk, wide leaves and normal fertility. The hybrid offspring of B73 wild-type maize (ZmPLD3 gene was not mutated) and the inbred line Mo17 was used as control.

Figure 3:
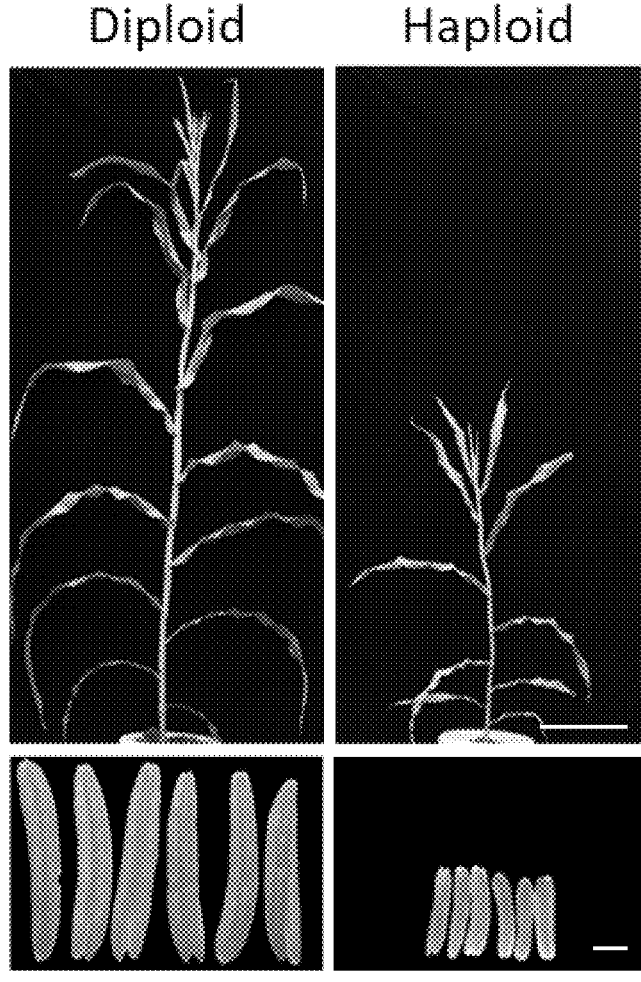
FIG. 3 is the diploid plant and its anther and the haploid plant and its anther in the hybrid progeny obtained by crossing homozygous gene mutant line zmpld3-1 to inbred line Mo17.

The observation results were shown in FIG. 3. The upper left and lower left pictures showed the heterozygous diploid plant and its anthers, which was from the hybrid progeny of the T1 transgenic homozygous mutant line zmpld3-1 and the inbred line Mo17; the upper right and lower right pictures showed the haploid candidate from the hybrid offspring and its anthers.

The results showed that 2 haploid candidates identified by polymorphic molecular markers and flow cytometry in the hybrid progeny of zmpld3-1 and Mo17 both were identified as maternal haploid after phenotypic identification.

Therefore, among the hybrid offspring individuals of the T1 homozygous mutant line zmpld3-1 and Mo17, the plant was considered as a haploid candidate if it was identified as a haploid by any one of the three aforesaid methods; if the plant was not identified as a haploid by three aforesaid methods, it was not a candidate for maternal haploid.

Haploid induction rate (%)=(number of haploid plants/ total number of tested plants)*100%= (2/195)*100%=1.02%, which could come to a conclusion that maternal haploids could be obtained by crossing the individuals with ZmPLD3 gene mutation to other materials.

INDUSTRIAL APPLICATION

The present invention discloses a new gene ZmPLD3 for inducing maize maternal haploids and its application. CRISPR/Cas9 technology is used to knock out the ZmPLD3 gene in maize to obtain transgenic homozygous mutant plants or its offspring, and they can be used as the male parent to cross with other maize materials to produce maize maternal haploid. The present invention obtained a series of allelic mutations of the gene ZmPLD3 for the first time, and proved its maternal haploid induced function through hybridization. The experiments of the present invention proved that the mutation of maize phospholipase PLD3 could lead to the production of maize maternal haploid, which provides new ideas for revealing the biological role of phospholipase in maize maternal haploid induction process. At the same time, the mutant individuals obtained by the present invention have the haploid induction ability in maize, which is of great significance for breeding new types of haploid induction lines with high haploid induction rate and improving the efficiency of maize haploid breeding.

The invention claimed is:

1. A method for inducing maternal haploids, comprising the following steps:
   (1) silencing or knocking out a ZmPLD3 gene in a target plant genome to obtain a transgenic plant;
   (2) crossing the transgenic plant obtained in step (1) as a male parent with female plants to obtain hybrid offspring which are maternal haploids;
   wherein the ZmPLD3 gene according to step (1) is any one of the following DNA molecules:
   (1) a DNA molecule whose genome sequence is as shown in SEQ ID NO: 1 of the sequence listing; and
   (2) a DNA molecule that originated from maize, whose sequence is at least 90%, identical to the DNA sequence defined in (1) and with the same function, wherein the plant is maize.

2. The method according to claim 1, wherein silencing or knocking out the ZmPLD3 gene in the target plant genome, comprises mutating the ZmPLD3 gene in the target plant genome to reduce an expression of the ZmPLD3 gene in the target plant genome or cause the ZmPLD3 gene in the target plant genome to lose function.

3. The method according to claim 2, wherein reducing the expression of the ZmPLD3 gene in the target plant genome or causing the ZmPLD3 gene in the target plant genome to lose function comprises mutating a first exon and/or a second exon and/or a third exon of the ZmPLD3 gene in the target plant genome; wherein the mutation is at least one of a deletion mutation, an insertion mutation, and a substitution mutation.

4. The method according to claim 3, wherein the mutation comprises inserting the base T between the 2205$^{th}$ base and the 2206$^{th}$ base of the 5' end of the ZmPLD3 gene in the target plant genome.

5. The method according to claim 3, wherein the mutation is achieved by CRISPR/Cas9 gene editing technology; and wherein a target sequence of the CRISPR/Cas9 is shown in SEQ ID NO: 2 of the sequence listing.

6. The method according to claim 1, wherein step (2) further comprises the following steps of:
   screening individual plants of the hybrid progeny by at least one method selected from the group consisting of haploid phenotypic identification, leaf ploidy identification and molecular marker identification to identify haploid plants; and
   selecting the individual plants of the hybrid progeny identified as haploid as maternal haploids.

7. A method for preparing a maternal haploid induction line comprising silencing or knocking out a ZmPLD3 gene in the target plant genome to obtain a transgenic plant comprising a plant maternal haploid induction line;
   the ZmPLD3 gene is any one of the following DNA molecules:
   (1) a DNA molecule whose genome sequence is as shown in SEQ ID NO: 1 of the sequence listing; and
   (2) a DNA molecule that originated from maize, whose sequence is at least 90%, identical to the DNA sequence defined in (1) and with the same function, and wherein the plant is maize.

8. The method according to claim 7, wherein silencing or knocking out the ZmPLD3 gene comprises:
   mutating the ZmPLD3 gene in the target plant genome to reduce an expression of the ZmPLD3 gene in the target plant genome or cause the ZmPLD3 gene in the target plant genome to lose function.

9. The method according to claim 8, wherein reducing the expression of the ZmPLD3 gene in the target plant genome or causing the ZmPLD3 gene in the target plant genome to lose function comprises:

mutating at least one of a first exon and/or a second exon and/or a third exon of the ZmPLD3 gene in the target plant genome, wherein the mutation is at least one of a deletion mutation, an insertion mutation, and a substitution mutation.

10. The method according to claim 9, wherein the mutation comprises inserting the base T between the $2205^{th}$ base and the $2206^{th}$ base of the 5' end of the ZmPLD3 gene in the target plant genome.

11. The method according to claim 10, wherein the mutation is achieved by CRISPR/Cas9 gene editing technology; and wherein a target sequence of the CRISPR/Cas9 is shown in SEQ ID NO: 2 of the sequence listing.

\*   \*   \*   \*   \*